(12) United States Patent
Liang et al.

(10) Patent No.: US 11,630,514 B2
(45) Date of Patent: Apr. 18, 2023

(54) BRAINWAVE FEEDBACK SYSTEM AND OPERATION METHOD THEREOF

(71) Applicant: NATIONAL CHENG KUNG UNIVERSITY, Tainan (TW)

(72) Inventors: Sheng-Fu Liang, Tainan (TW); Fu-Zen Shaw, Tainan (TW); Chih-En Kuo, Tainan (TW); Yung-Hung Wang, Taipei (TW); Tsung-Hua Lu, Tainan (TW); Tsung-Hao Hsieh, Taichung (TW); Tai-Jie Yun, Taichung (TW); Jen Jui Hsueh, Tainan (TW); I Yu Chen, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 196 days.

(21) Appl. No.: 16/886,636

(22) Filed: May 28, 2020

(65) Prior Publication Data
US 2021/0333878 A1    Oct. 28, 2021

(30) Foreign Application Priority Data
Apr. 24, 2020   (TW) ................................ 109113808

(51) Int. Cl.
*G06F 3/01*      (2006.01)
*G16H 10/20*     (2018.01)
(Continued)

(52) U.S. Cl.
CPC ............ *G06F 3/015* (2013.01); *A61B 5/0006* (2013.01); *A61B 5/375* (2021.01); *G10L 15/22* (2013.01);
(Continued)

(58) Field of Classification Search
CPC ......... G06F 3/015; G16H 10/20; A61B 5/375; A61B 5/0006; G10L 15/22; G10L 2015/225
See application file for complete search history.

(56) References Cited

U.S. PATENT DOCUMENTS

| | | | |
|---|---|---|---|
| 8,442,626 B2 | 5/2013 | Zavoronkovs et al. | |
| 2011/0313308 A1* | 12/2011 | Zavoronkovs | A61B 5/165 600/544 |
| 2014/0223462 A1* | 8/2014 | Aimone | H04N 21/4307 725/10 |

FOREIGN PATENT DOCUMENTS

TW    M474488 U    3/2014

OTHER PUBLICATIONS

TW Office Action in Application No. 109113808 dated Sep. 4, 2020.

* cited by examiner

*Primary Examiner* — Robert J Michaud
(74) *Attorney, Agent, or Firm* — Maschoff Brennan

(57) ABSTRACT

A brainwave feedback system, adapted to generate feedback based on a user's brainwave, the brainwave feedback system comprises: a brainwave sensing device, configured to obtain a first brainwave signal of the user; a server, storing a keyword string pool including a plurality of sorted keywords, and performing a feedback procedure when a first physiological parameter falls outside of a predetermined parameter range, wherein the first physiological parameter is associated with the first brainwave signal, the feedback procedure includes choosing a keyword from the keyword string pool by the server as a feedback keyword, and outputting the feedback keyword; and an output component, in communicable connection with the server, wherein the output component presents an analysis result corresponding to the first physiological parameter. The present disclosure
(Continued)

further discloses an operation method of brainwave feedback system.

20 Claims, 6 Drawing Sheets

(51) Int. Cl.
  *A61B 5/00* (2006.01)
  *G10L 15/22* (2006.01)
  *A61B 5/375* (2021.01)
(52) U.S. Cl.
  CPC ....... G16H 10/20 (2018.01); *G10L 2015/225* (2013.01)

BRAINWAVE FEEDBACK SYSTEM AND OPERATION METHOD THEREOF

CROSS-REFERENCE TO RELATED APPLICATIONS

This non-provisional application claims priority under 35 U.S.C. § 119(a) on Patent Application No(s). 109113808 filed in Republic of China on Apr. 24, 2020, the entire contents of which are hereby incorporated by reference.

BACKGROUND

1. Technical Field

This disclosure relates to a brainwave feedback system and operation method thereof, particularly to a feedback system and its operation method performing a feedback procedure.

2. Related Art

Nowadays, people often have sleeping problems such as insomnia. Insomnia includes having difficulty falling asleep, light sleep and difficulty in continuing one's sleep. Insomnia not only affects one's daily activities and work efficiency, but also causes mental disorders such as depression or anxiety. Medication is currently the main approach of treating chronic insomnia. Although most sleep aid medicine (for example, sleeping pills) can help insomnia patients fall asleep more easily, it is still difficult for insomnia patients to enter deep sleep just by taking sleep aid medicine. Sleep aid medicine fails to improve one's sleep qualities nor provide sufficient duration of deep sleep. Further, long-term usage of sleep aid medicine is more likely to cause bioaccumulation.

Since sleeping pills can't improve insomnia efficiently and fundamentally, many sleep aid devices came into being. Most sleep aid devices use, for example, sound or light stimulation, or electrical stimulation to the brain to help user fall asleep. However, when the user is having insomnia, the user may instead be more sensitive to the outside world. Therefore, the stimulations provided by these sleep aid devices may be extra disturbance when the user is falling asleep or trying to fall asleep. The user may even be awakened by these stimulations when he or she is in a light sleep stage.

SUMMARY

Accordingly, this disclosure provides a brainwave feedback system and operation method of thereof to solve the above-mentioned concerns.

According to one or more embodiment of this disclosure, a brainwave feedback system, adapted to generate feedback based on a user's brainwave, the brainwave feedback system comprising: a brainwave sensing device, configured to obtain a first brainwave signal of the user; a server, storing a keyword string pool including a plurality of sorted keywords, and performing a feedback procedure when a first physiological parameter falls outside of a predetermined parameter range, wherein the first physiological parameter is associated with the first brainwave signal, and the feedback procedure includes choosing a keyword from the keyword string pool by the server as a feedback keyword and outputting the feedback keyword; and an output component, in communicable connection with the server, wherein the output component presents an analysis result corresponding to the first physiological parameter.

According to one or more embodiment of this disclosure, an operation method of brainwave feedback system, adapted to a brainwave feedback system, wherein the brainwave feedback system is configured to generate feedback based on a user's brainwave, and the brainwave feedback system comprises a mobile device, a server and a brainwave sensing device, with the operation method comprising: presenting a questionnaire by the mobile device and obtaining a reply corresponding to the questionnaire; performing a language processing procedure on the reply by the server to capture a plurality of keywords from the reply; sorting the keywords according to a result of the language processing procedure by the server to obtain a keyword string pool; obtaining a first brainwave signal of the user by the brainwave sensing device and outputting the first brainwave signal to the mobile device; obtaining a first physiological parameter corresponding to the first brainwave signal based on the first brainwave signal by the mobile device; determining whether the first physiological parameter falls outside of a predetermined parameter range by the mobile device; and performing a feedback procedure by the mobile device when determining the first physiological parameter falls outside of the predetermined parameter range, wherein the feedback procedure includes controlling the server by the mobile device to choose a keyword from the keyword string pool as a feedback keyword, and output the feedback keyword to the mobile device for the mobile device to present the feedback keyword.

In view of the above description, the brainwave feedback system and operation method according to one or more embodiments of the present disclosure may help users reduce the frequency of taking sleeping pills or other medications of above mentioned syndromes to avoid problems such addiction and bioaccumulation caused by drugs. In addition, the brainwave feedback system and operation method according to one or more embodiments of the present disclosure may further avoid the stimulation presented by the sleep aid device which in turn causes sleeping disturbance when the user is falling asleep or trying to fall asleep. The brainwave feedback system of the present disclosure may be applied in a home environment, and does not limit the timing of using the brainwave feedback system. Therefore, not only that users don't have to visit specific research institute such as a hospital to use the brainwave feedback system, users can also use the brainwave feedback system consciously during their daily routines. Therefore, users can apply the experiences gained from training when they are trying to fall asleep to achieve the effect of falling asleep quickly, thereby avoiding the situation of using external assistance to help users fall asleep.

BRIEF DESCRIPTION OF THE DRAWINGS

The present disclosure will become more fully understood from the detailed description given hereinbelow and the accompanying drawings which are given by way of illustration only and thus are not limitative of the present disclosure and wherein.

DETAILED DESCRIPTION

Figure 1:
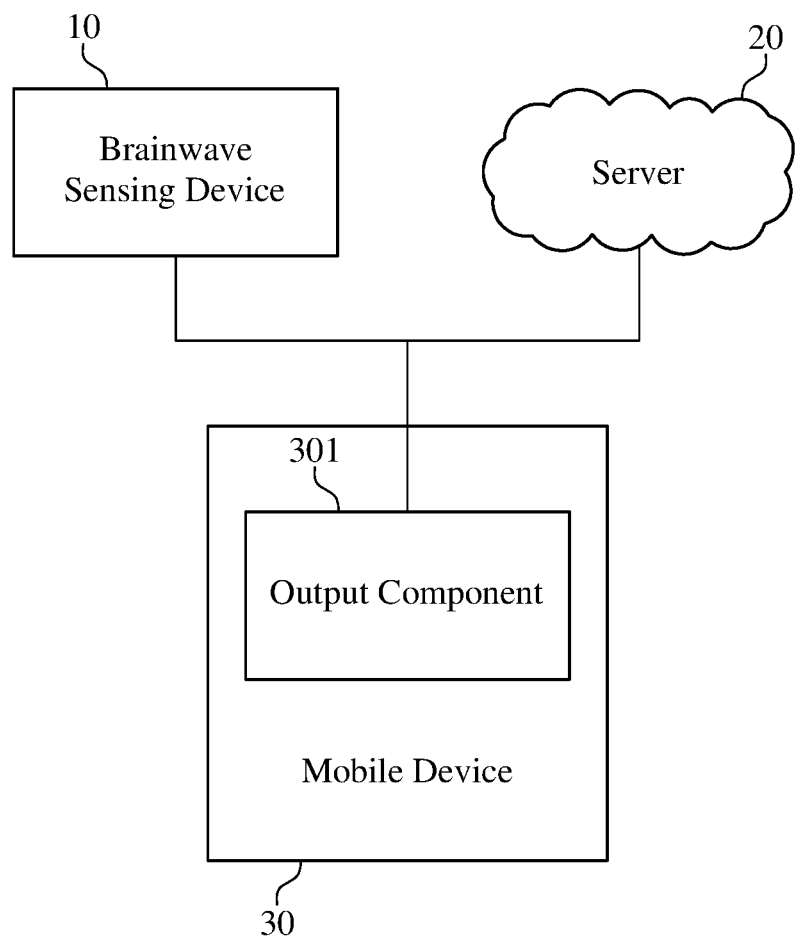
FIG. 1 is a block diagram of a brainwave feedback system according to an embodiment of the present disclosure.

Please refer to FIG. 1 which is a block diagram of a brainwave feedback system according to an embodiment of the present disclosure. The brainwave feedback system of the present disclosure includes at least a brainwave sensing device 10 and a server 20, wherein the brainwave sensing device 10 is configured to obtain signals, and the server 20 can be used to process and analyze the signals obtained by the brainwave sensing device 10. The brainwave feedback system of the present disclosure can also further include a mobile device 30, wherein the mobile device 30 can replace the server 20 to process and analyze the signals obtained by the brainwave sensing device 10, and the server 20 is configured to store related data and results of signal processing, the present disclosure is not limited thereto.

The present disclosure does not limit the actual timing of using the brainwave feedback system, a user does not have to wait until a certain time to use the brainwave feedback system. In detail, the user can use the brainwave feedback system consciously as their daily routines to train themselves on how to quickly shift their brainwave into a desired state. These desired states of brainwaves are not limited to brainwaves in a relaxed or falling-asleep state, the desired states also include brainwaves during implicit mental states such as when concentrating or focusing. Accordingly, the experience gained during training can be applied when the user wants to enter the desired state of brainwaves, to achieve shifting brainwaves into the desired state faster, and to avoid shifting brainwaves into the desired state by using external assistance (for example, medications, radio wave treatment, etc.).

The brainwave sensing device 10 of the present disclosure preferably includes dry electrodes to obtain a first brainwave signal. The server 20 is preferably a cloud server, the server 20 stores a keyword string pool including a plurality of sorted keywords, the keyword string pool preferably is stored in a user log of the server 20. The keyword string pool includes the plurality of keywords, which are preferably arranged in sequence or in priority orders. The server 20 performs a feedback procedure when a first physiological parameter falls outside of a predetermined parameter range, wherein the first physiological parameter is associated with the first brainwave signal, and the first physiological parameter can be calculated by the brainwave sensing device 10 based on the first brainwave signal.

The feedback procedure includes choosing a keyword from the keyword string pool by the server 20 as a feedback keyword. That is, the server 20 uses the keyword sequenced first in the keyword string pool as the feedback keyword. The server 20 can remove this keyword from the keyword string pool or move this keyword to the end of the keyword string pool after outputting the feedback keyword. The server 20 preferably outputs the feedback keyword to the mobile device 30 for an output component 301 to present the feedback keyword. The mobile device 30 is, for example, a mobile phone, a tablet, etc., the output component 301 is, for example, a display screen, a speaker of the mobile device 30, or a headset connecting the mobile device 30. The present disclosure does not limit the type of output component 301.

Figure 2:
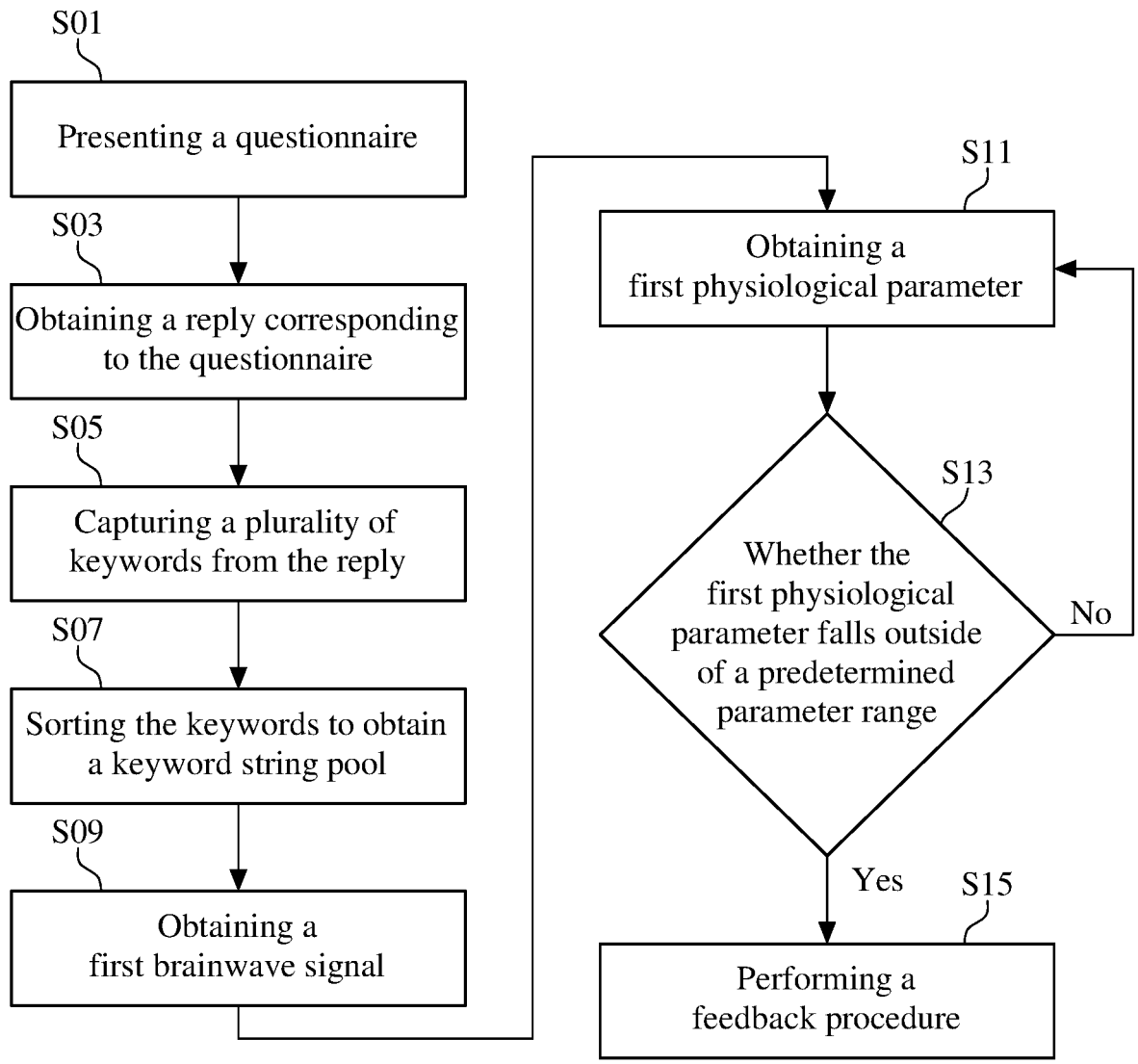
FIG. 2 is a flow chart of an operation method of brainwave feedback system according to an embodiment of the present disclosure.

In order to explain the present disclosure in more detail, please refer to both FIGS. 1 and 2, wherein FIG. 2 is a flow chart of an operation method of brainwave feedback system according to an embodiment of the present disclosure. It should be noted that, in order for the brainwave feedback system of the present disclosure to better protect user's privacy, steps S11 and S13 in FIG. 2 are preferably performed by the mobile device 30. However, steps S11 and S13 can also be performed by the server 20, the present disclosure does not limit the device that performs steps S11 and S13.

Step S01: presenting a questionnaire.

The server 20 can pre-store a questionnaire, and outputs the questionnaire to the mobile device 30 so that the mobile device 30 can present the questionnaire by the output component 301, and the content of the questionnaire is preferably related to questions about various scenarios/situations. For example, when the brainwave feedback system of the present disclosure is applied to treat insomnia, the questions of the questionnaire may include question 1: "What do you usually do when you are alone?", question 2: "Do you have a memorable experience about traveling?", question 3: "What do you think about the most when having insomnia?", and question 4: "Is there anything you want to purchase recently?" etc. When the output component 301 is the display screen of the mobile device 30, the output component 301 can present the questionnaire by displaying it on the display screen; when the output component 301 is the speaker or headset connecting the mobile device 30, the output component 301 can present the questionnaire by outputting it in the form of audio.

Step S03: obtaining a reply corresponding to the questionnaire.

After the output component 310 presents the questionnaire, the mobile device 30 then can obtain a reply corresponding to the previously described questionnaire inputted by the user, and output the reply to the server 20. For example, the reply corresponding to question 1 can be: "I enjoying having a piece of cake while watching TV shows the most when I'm alone"; the reply corresponding to question 2 can be: "The most memorable experience about traveling I have is when traveling in Japan"; the reply corresponding to question 3 can be: "I think about work the most when having insomnia"; the reply corresponding to question 4 can be: "Recently I want to purchase a new mobile phone".

Please refer to steps S01 and S03 together, the questionnaire presented by the mobile device 30 preferably contains timing and affirmative reminders, to remind the user that the provided replies are preferably life experiences during the last 3 months, and to further provide the affirmative the user has for each reply. Take the reply of "I enjoying having a piece of cake while watching TV shows the most when I'm alone" as an example, the reply provided by user is preferably a life experience the user had within the past 3 months, the user then provides an affirmative score for this reply. Assuming the highest affirmative score is "10", and when the affirmative score provided by the user is "2", it indicates that this reply may not be a useful reply for the brainwave feedback training. On the contrary, when the affirmative score provided by the user is "9", that means this reply may be of great use later on during the brainwave feedback training.

Step S05: deriving a plurality of keywords from the reply.

After obtaining the reply, the server 20 performs a language processing procedure on the reply to perform word segmentation and word analysis to derive the keywords. The server 20 preferably performs natural language processing (NLP) on the reply. The server 20 can perform natural language processing by using Natural Language Frame Semantics Parser developed by Google, and Chinese Knowledge and Information Processing (CKIP) techniques developed by Academia Sinica of Taiwan.

The way of the server 20 deriving keywords from the reply is, for example, by tokenizing, and to truncate the reply into multiple words according to characteristics of the words, such as emotion, timing, goal, degree, theme and owner. The words can be connected to each other based on the characteristic, the server 20 can use one or more of the words as keywords.

Take the reply of question 1 above for example, the derived keyword based on emotion is "like"; the derived keyword based on timing is "when"; the derived keyword based on goal is "having"; the derived keyword based on degree is "the most"; the derived keywords based on theme are "cake" and "TV shows"; the derived keyword based on owner is "I". Similarly, the derived keywords from the reply of question 2 are, for example, "memorable experience about traveling" and "Japan"; the derived keywords from the reply of question 3 are, for example, "insomnia" and "work"; the derived keywords from the reply of question 4 are, for example, "want to purchase" and "mobile phone".

Since these keywords are connected with each other, the server 20 can correspond "cake" to "alone" of question 1; "Japan" to "memorable experience about traveling" of question 2; "work" to "insomnia" of question 3; and "mobile phone" to "want to purchase" of question 4.

Furthermore, the server 20 can have a database, and the keywords can be stored in the database based on their individual categories, wherein the categories preferably include "Food", "Clothing", "Housing", "Transportation", "Education", and "Entertainment", and the categories are constructed together as a semantic network. Take the reply of question 1 for example, the keywords obtained by performing the language processing procedure include "cake" and "TV shows", the server 20 can then create a keyword category corresponding to the keyword "cake" in the database. In detail, the keyword category can include the categories, instances, associations, etc. of the keywords, and the category of "cake" can be "Food"; the instance of "cake" can be "alone"; the associations of "cake" can be "Entertainment", which the keyword "TV shows" belongs, and the numbers of each keyword category can be one or more. Accordingly, the server 20 can find the appropriate keyword based on the keyword category.

Step S07: sorting the keywords to obtain a keyword string pool.

The server 20 can assign the corresponding keyword score to each keyword according to the result of the language processing procedure after receiving the keywords. For example, doing things alone (question 1) can be relaxing, so the keyword score of the keyword "cake" can be "5". A memorable traveling experience (question 2) provides relief, so the keyword score of the keyword "Japan" can be "3". The things one thinks about when having insomnia (question 3) may intensify insomnia, so the keyword score of the keyword "work" is "−1". And things one wants to purchase (question 4) may be exciting, so the keyword score of the keyword "mobile phone" can be "1". The server 20 then can sort the keywords "cake", "Japan", "work", and "mobile phone" based on their keyword scores to obtain the keyword string pool, and record the keyword string pool into the user log, wherein the keyword string pool is, for example, "cake-Japan-mobile phone".

In addition, sorting keywords can be achieved by using a user keyword ranking (UKR) equation. In detail, the UKR equation can be as below:

$$UKR(i) = (1 - d_i) + d_i \times \frac{\Sigma SKR}{WKR} + U_{record}$$

wherein, UKR(i) is a ranking(sequence) score of the keyword i; di is the affirmative score of the reply provided by the user; SKR is the ranking scores of other keywords in the semantic network that can be linked to the keyword i (for example, the keyword i is "cake", the keyword "TV shows" can be linked to the keyword "cake", therefore SKR can be the ranking score of the keyword "TV shows"); WKR is the sum of the weight of the connections between the keyword i and other keywords (for example, the keyword "cake" is strongly connected to both the keywords "TV shows" and "alone", therefore the WKR of the keyword "cake" is high; the connection between the keyword "work" and the keywords "TV shows" as well as the connection between the keyword "work" and the keyword "alone" are both weak, therefore the WKR of the keyword "work" is low); Urecord is the user's recent performance score of entering the desired state (for example, if the user tries to ease insomnia through the brainwave feedback system, then the recent performance score of entering the desired state is, for example, a score of user's recent sleeping quality), wherein Urecord can also include the user's satisfaction level of the result of brainwave training.

It should be noted that, when WKR is high, it means that the connections between the keyword i and other keywords are in dispersed state (unless SKR is also high, which means that other keywords connecting the keyword i have higher ranking scores). On the contrary, when WKR is low, it means that the connections between the keyword i and other keywords are concentrated on few keywords. Therefore, when WKR is low, if SKR is high (meaning that the user has similar views with other users using other keywords in the semantic network that can be linked to the keyword i), then UKR(i) is high (the ranking of keyword i rises faster); contrarily, if SKR is also low, then UKR(i) is low (the ranking of keyword i rises slower).

Please continue referring to the above UKR equation. If the UKR(i) of the keyword i is higher, then the keyword i is ranked higher in the keyword string pool. When the feedback received from the user after using the keyword i for training isn't ideal (UKR(i) is low) or is ideal (UKR(i) is high), the ranking score of the keyword can be updated using the UKR equation, so that the user can receive proper brainwave training.

The above mentioned SKR is a server keyword ranking. That is, SKR is the ranking scores of other keywords that can be linked to the keyword in the semantic network i. SKR(i) can be obtained using below equation:

$$SKR(i) = (1 - d_i) + d_1 \times \Sigma \frac{SKR}{WKR}$$

wherein, the equation of obtaining SKR(i) is similar to the user keyword ranking equation, the difference lies in that the equation of SKR(i) does not take Urecord into consideration, and di is a brainwave performance score after using the keyword i for training.

Further, if the above mentioned database stores multiple default keywords, the server 20 can also delete the default keywords relating to "work" from the database based on the keyword score of the keyword "work". For example, the server 20 may delete default keywords which are highly related to the keyword "work" based on the negative keyword score of the keyword "work". For instance, the default keywords related to the keyword "work" can include "achievement", "salary raise", and "promotion". Therefore, if the server 20 captures the keyword "work" from another user's reply, and that the keyword score of "work" is "3", and when the keywords in the keyword string pool corresponding to the another user are all used up, the server 20 can output the default keywords such as "achievement", "salary raise", and "promotion". On the contrary, when the keyword score of "work" is a negative number, the server 20 can delete at least one of the default keywords. For example, if the keyword score of "work" is "4", then the server 20 can delete "work" from the database; if the keyword score of "work" is "−5", the server 20 can delete not only "work" from the database, but also delete the default keywords such as "achievement", "salary raise", and "promotion".

Step S09: obtaining a first brainwave signal.

The brainwave sensing device 10 can sense the user's brainwave to obtain the first brainwave signal and output the first brainwave signal to the mobile device 30.

Step S11: obtaining a first physiological parameter.

The mobile device 30 can obtain the first physiological parameter corresponding to the first brainwave signal after obtaining the first brainwave signal. The mobile device 30 can further obtain an analysis result of the first physiological parameter, wherein the detailed description of the mobile device 30 obtaining the corresponding brainwave score based on the first physiological parameter will be further described below in FIG. 5A. In the present embodiment, the analysis result is the brainwave score, the analysis result can also be a determination result of whether the first physiological parameter fits a default standard. In addition, the brainwave sensing device 10 can also output the first brainwave signal to the server 20, so that the server 20 can obtain the corresponding analysis result of the first physiological parameter based on the first physiological parameter.

For example, if the user log does not have any records of using the brainwave feedback system, meaning this is the first time the user is using the brainwave feedback system. The mobile device 30 can adjust the brainwave score based on a usage history stored in the user log. In other words, when a usage times of using the brainwave feedback system in the usage history is lower than a threshold number, the mobile device 30 increases the brainwave score by a predetermined increment, wherein the predetermined increment is inversely related to the usage times in the usage history, and the threshold number is, for example, three times. When the usage times of using the brainwave feedback system in the usage history reaches the threshold number, the mobile device 30 does not adjust the brainwave score. Meaning, the mobile device 30 can give different weight values according to the usage history stored in the user log. For instance, when the usage times is below the threshold number, the mobile device 30 multiplies the original brainwave score by a weight value higher than 1; when the usage times reaches the threshold number, the mobile device 30 does not adjust the original brainwave score, or multiplies the original brainwave score by a weight value lower than 1 to calculate the subsequent outputted brainwave score.

Besides, the mobile device 30 can also use physical properties such as amplitude, frequency of the first brainwave signal as the first physiological parameter, and convert the first physiological parameter to the brainwave score.

Step S13: determining whether the first physiological parameter falls outside of a predetermined parameter range.

The mobile device 30 determines whether the first physiological parameter falls outside of the predetermined parameter range after obtaining the first physiological parameter, wherein the predetermined parameter range is, for example, a range composed of physiological parameters of the brainwave in a relaxed state. That is, the predetermined parameter range is, for example, a range composed of physical properties (such as amplitudes, frequencies) of the brainwave in an ideal state, wherein when the predetermined parameter is frequency, the predetermined parameter range of the brainwave in the relaxed state is preferably 8 Hz to 13 Hz. The present disclosure does not limit the predetermined parameter range.

Further, the mobile device 30 can also determine whether the first physiological parameter falls outside of the predetermined parameter range based on the brainwave score. In other words, the predetermined parameter range can have a corresponding predetermined score, the mobile device 30 can compare the brainwave score and the predetermined score to determine whether the first physiological parameter falls outside of the predetermined parameter range.

When the mobile device 30 determines that the first physiological parameter does not fall outside of the predetermined parameter range and/or the brainwave score does not reach the predetermined score, the brainwave sensing device 10 performs step S09 to continue obtaining the brainwave signals to observe whether the brainwave signal of the user gets closer to or further away from the ideal brainwave signal as time progresses. On the contrary, when the mobile device 30 determines that the first physiological parameter falls outside of the predetermined parameter range, the mobile device 30 performs step S15: performing a feedback procedure.

Figure 3:
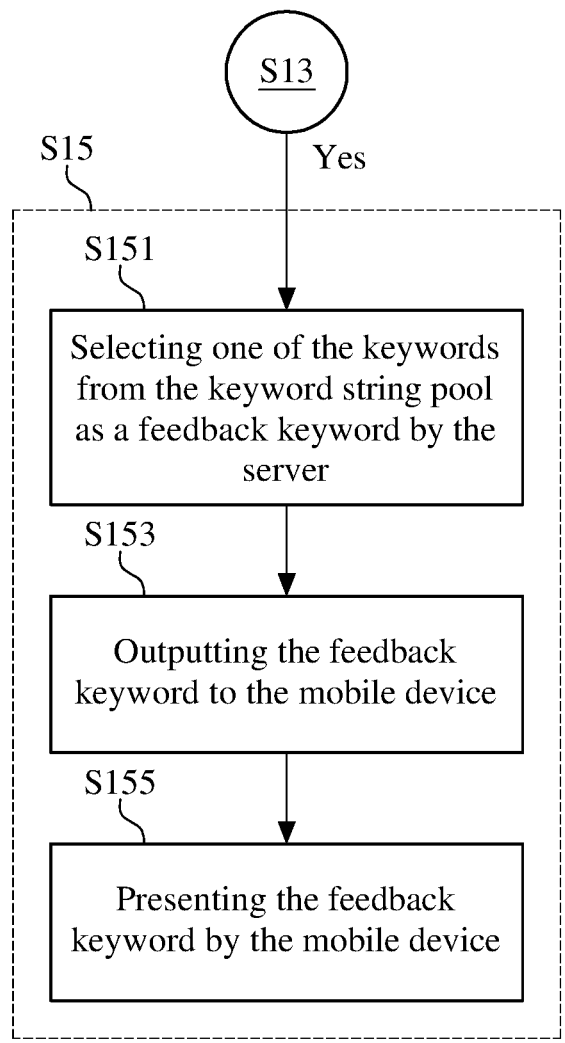
FIG. 3 is a flow chart of feedback procedure according to an embodiment of the present disclosure.

Please refer to both FIGS. 1 and 3, wherein FIG. 3 is a flow chart of feedback procedure according to an embodiment of the present disclosure.

The feedback procedure shown in step S15 of FIG. 2 can comprise the following sub-steps.

Step S151: selecting one of the keywords from the keyword string pool as a feedback keyword by the server 20.

Take the above "cake-Japan-mobile phone" keyword string pool as an example, when the first physiological parameter falls outside of the predetermined parameter range (step S15), that means the brainwave of the user hasn't reached the ideal state (if the brainwave feedback system is used to alleviate insomnia, then the ideal state is, for example, brainwave in a relaxed state). Therefore, the server 20 can select the first ranked keyword "cake" from the keyword string pool as the feedback keyword.

Moreover, the server 20 can also select a keyword from another keyword string pool as the feedback keyword. For example, the another keyword string pool can be obtained from a previous questionnaire, or keyword string pool stored in another user log. The present disclosure is not limited thereto.

In detail, when the server 20 selects the feedback keyword from the another keyword string pool, the server 20 can determine which keyword(s) to avoid according to the keyword score(s). For example, since the keyword "work" has relatively low keyword score, the server 20 can avoid selecting keywords related to "work" when selecting the feedback keywords from the another keyword string pool.

Step S153: outputting the feedback keyword to the mobile device 30.

The server 20 outputs the feedback keyword to the mobile device 30 after selecting the feedback keyword.

Step S155: presenting the feedback keyword by the mobile device 30.

Take the above mentioned "cake" as an example, the mobile device 30 can present the feedback keyword by the output component 301, and when the output component 301 is the screen of the mobile device 30, the mobile device 30 can display the word "cake" on its screen; when the output component 301 is the speaker or headset of the mobile device 30, the mobile device 30 can output the word "cake" through the output component 301 in an audio form.

Moreover, please refer back to step S09 of FIG. 2, before the brainwave sensing device 10 obtains the first brainwave signal, the mobile device 30 can obtain and present the feedback keyword from the server 20 to help the user shift their brainwaves into the relaxed state. Accordingly, when there is a difference between the first brainwave signal and the brainwave signal in the relaxed state, the user can imagine the feedback keyword by using the feedback keyword as a reminder, so as to train the user to shift their brainwave signal closer to the brainwave signal in the relaxed state by imaging the feedback keyword.

Figure 4:
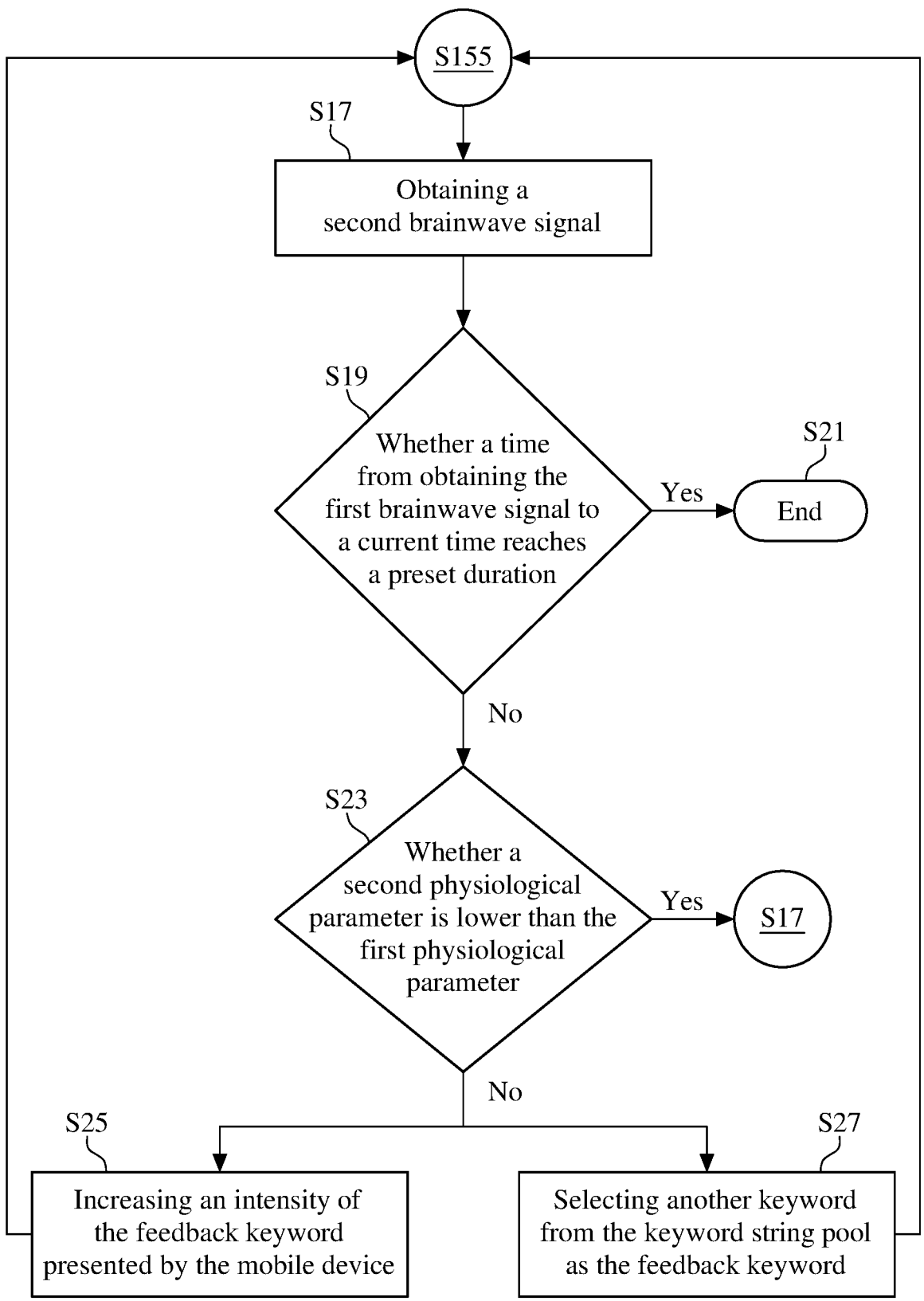
FIG. 4 is a flow chart of an operation method of brainwave feedback system according to another embodiment of the present disclosure.

Please refer to both FIGS. 1 and 4, wherein FIG. 4 is a flow chart of an operation method of brainwave feedback system according to another embodiment of the present disclosure.

After the mobile device 30 presents the feedback keyword (step S155 of FIG. 3), the operation method of the present disclosure can further continue to the following steps.

Step S17: obtaining a second brainwave signal.

Step S19: determining whether a time from obtaining the first brainwave signal to a current time reaches a preset duration.

Please refer to steps S17 and S19 together. The mobile device 30 obtaining the second brainwave signal is for determining whether the user's brainwave signal is closer to the relaxed state after the feedback procedure; and step S19 is for determining whether the time from the brainwave sensing device 10 obtaining the first brainwave signal (step S09 of FIG. 2) to the current time exceeds the preset duration. When the time from the brainwave sensing device 10 obtaining the first brainwave signal to the current time exceeds the preset duration, ends the method (step S21) so as to avoid the training time being dragged too long, wherein the preset duration is, for example, 6 minutes. The present disclosure is not limited thereto.

When it is determined that the time from the brainwave sensing device 10 obtaining the first brainwave signal to the current time does not exceed the preset duration in step S19, continues to step S23: determining whether a second physiological parameter is lower than the first physiological parameter.

Similarly, the mobile device 30 obtains the second physiological parameter based on the second brainwave signal, and compares the first physiological parameter and the second physiological parameter to generate a comparison result, wherein the obtaining the second physiological parameter based on the second brainwave signal and comparing the first physiological parameter and the second physiological parameter to generate the comparison result can also be performed by the server 20, the present disclosure is not limited thereto. For example, the mobile device 30 compares the first and second physiological parameters can be comparing the brainwave scores of the first and second physiological parameters so as to determine whether the second brainwave signal, comparing to the first brainwave signal, is closer to the brainwave signal in the relaxed state after the feedback procedure is performed.

Further, the mobile device 30 can also update the brainwave score of the second physiological parameter. That is, when the second physiological parameter is lower than the first physiological parameter, it means that the performance of the brainwave signal declines. Therefore, the mobile device 30 can lower the brainwave score of the second physiological parameter to inform the user that the second brainwave signal comparing to the first brainwave signal is further away from the brainwave signal in the relaxed state.

When the mobile device 30 determines that the second physiological parameter is higher than the first physiological parameter, it means that the second brainwave signal comparing to the first brainwave signal is closer to the brainwave signal in the relaxed state. Therefore, step S17 is then performed to continue obtaining brainwave signals until preset duration is achieved.

On the contrary, when the mobile device 30 determines that the second physiological parameter is not lower than the first physiological parameter, step S25 or step S27 is then performed.

Step S25: increasing an intensity of the feedback keyword presented by the mobile device.

When the comparison result is that the second physiological parameter is lower than the first physiological parameter, it means that the second brainwave signal, comparing to the first brainwave signal, is not closer to the brainwave signal in the relaxed state. Therefore, the server 20 can control the mobile device 30 based on the comparison result to increase the intensity of presenting the feedback keyword. For example, the mobile device 30 can increase the clarity of the feedback keyword displayed on its screen, or increase the time of the feedback keyword displayed on its screen. The mobile device 30 can also increase the intensity of presenting the feedback keyword by increasing the frequency of presenting the feedback keyword in an audio signal. The present disclosure is not limited thereto.

Further, if the usage times of the brainwave feedback system in the user log reaches the threshold number, and the second physiological parameter is not lower than the first physiological parameter, the server 20 can also control the mobile device 30 to increase the intensity of presenting the feedback keyword.

Step S27: selecting another keyword from the keyword string pool as the feedback keyword.

Similarly, the server 20 can select another keyword from the keyword string pool as the feedback keyword. Take the "cake-Japan-mobile phone" keyword string pool as an example, the original feedback keyword is "cake". However, after the mobile device 30 presents the keyword "cake", the second physiological parameter is lower than the first physiological parameter, which means that the keyword "cake" does not contribute to the user being closer to the relaxed state. Therefore, the server 20 can select "Japan" as the feedback keyword.

In addition, if the server 20 already controls the mobile device 30 to increase the intensity of presenting the feedback keyword, and the other three physiological parameters obtained after the second physiological parameter still fall outside of the predetermined parameter range, the server 20 can also select another keyword from the keyword string pool as the feedback keyword.

Or, the user expects to, for example, alleviate insomnia, and the mobile device 30 already stores a sleeping quality parameter (for example, frequency of the brainwave signal during the user's sleep) of the user obtained by a sleeping sensor. Then after the user has used the brainwave feedback system for a week, if the user's sleeping quality is still determined as not ideal for over 3 times or for consecutive 2 days based on the sleeping quality parameter (for example, Urecord is ranged from 1 to 100, and Urecord may be lower than 70 when the sleeping quality is determined not ideal), the server 20 can also select another keyword from the keyword string pool as the feedback keyword.

Please continue referring to step S27, besides, the server 20 can further decrease the keyword score of the keyword "cake" and/or increase the keyword score of the keyword "Japan" (the raking score of the keyword, UKR) to update the rankings of the keywords in the keyword string pool.

After steps S25 or S27, the mobile device 30 can present the feedback keyword or the another feedback keyword with the updated intensity in step S155.

Further, after performing the feedback procedure, the mobile device 30 can also present the feedback questionnaire to obtain the corresponding feedback reply. The feedback questionnaire includes questions such as "How do you feel after the brainwave training?". And the feedback reply inputted by the user can be, for example, "I'm feeling more relaxed.", or "I'm feeling more anxious."

Similar to the above described questionnaire, the server 20 can also perform the language processing procedure on the feedback questionnaire to capture keywords and to determine whether to adjust the sequence of the keywords in the keyword string pool accordingly.

For example, when the feedback reply is "I'm feeling more relaxed.", the keyword derived by the server 20 after performing the language processing procedure can be "more relaxed". The server 20 can then not adjust the sequence of the keyword in the keyword string pool. When the feedback reply is "I'm feeling more anxious.", the keyword derived by the server 20 after performing the language processing procedure can be "more anxious". The server 20 can then adjust the sequence of the keyword in the keyword string pool so as to update the keyword string pool to avoid using the keyword that makes the user become more anxious in the next feedback procedure. That is, the server 20 can update the UKR(i) of the keyword i according to the feedback reply. In addition, the server 20 can also determine whether to adjust the sequence of the keyword in the keyword string pool according to the sleeping quality of the user. For example, the server 20 can receive the sleeping quality parameter from the sleeping sensor to determine whether the sleeping quality of the user has improved after the training. When the server 20 determines the sleeping quality has improved, then the server 20 can choose not to adjust the sequence of the keyword in the keyword string pool; when the server 20 determines the sleeping quality hasn't improved or has deteriorated, then the server 20 can adjust the sequence of the keyword in the keyword string pool to avoid using the keyword that makes the user become more anxious in the next feedback procedure.

The mobile device 30 can also determine whether to adjust the predetermined parameter range according to the sleeping quality of the user. For example, when the mobile device 30 learns that the user's recent sleeping quality isn't ideal, then it means there's a greater chance that the user's brainwave signal may not be close to the brainwave signal in the relaxed state when using the brainwave feedback system. Therefore, the mobile device 30 can increase the range of the predetermined parameter range, or as mentioned above, offer a higher weight value. Thus, when comparing the first physiological parameter to the predetermined parameter range, a higher tolerance is created to prevent the user from being affected by the information that the brainwave signal is not ideal.

Or, when the user log stores multiple records of using the brainwave feedback system, the mobile device 30 can also narrow down the range of the predetermined parameter range, so that the brainwave signal can be closer to the relaxed state after multiple experiences.

Figure 5A:
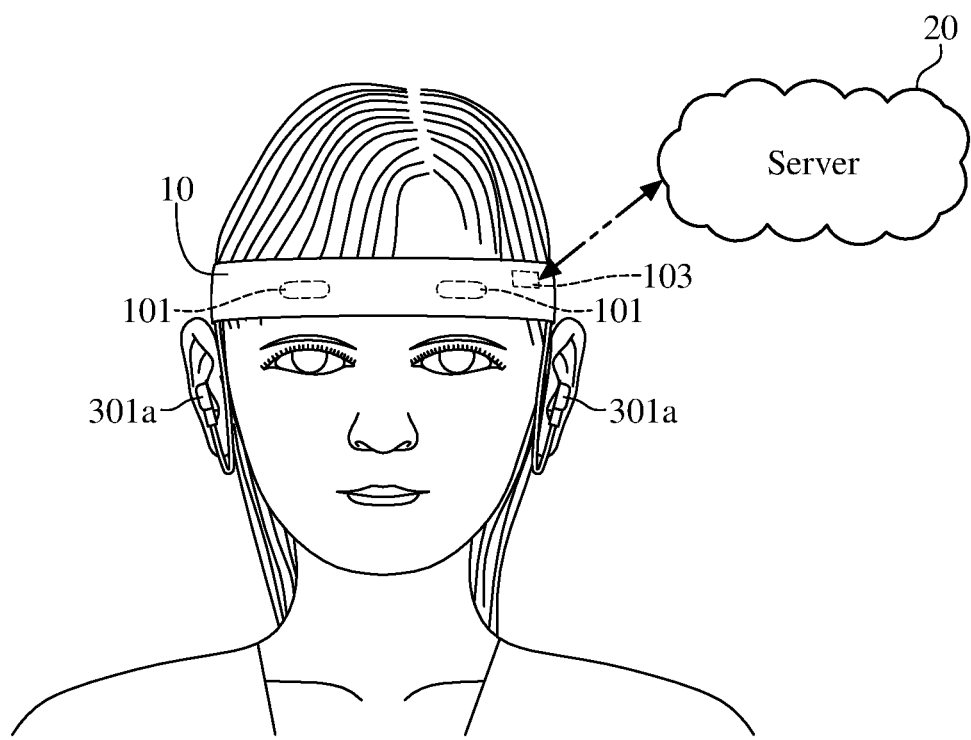
FIGS. 5A and 5B are diagrams of scenarios of using the brainwave feedback system according to an embodiment of the present disclosure.
Figure 5B:
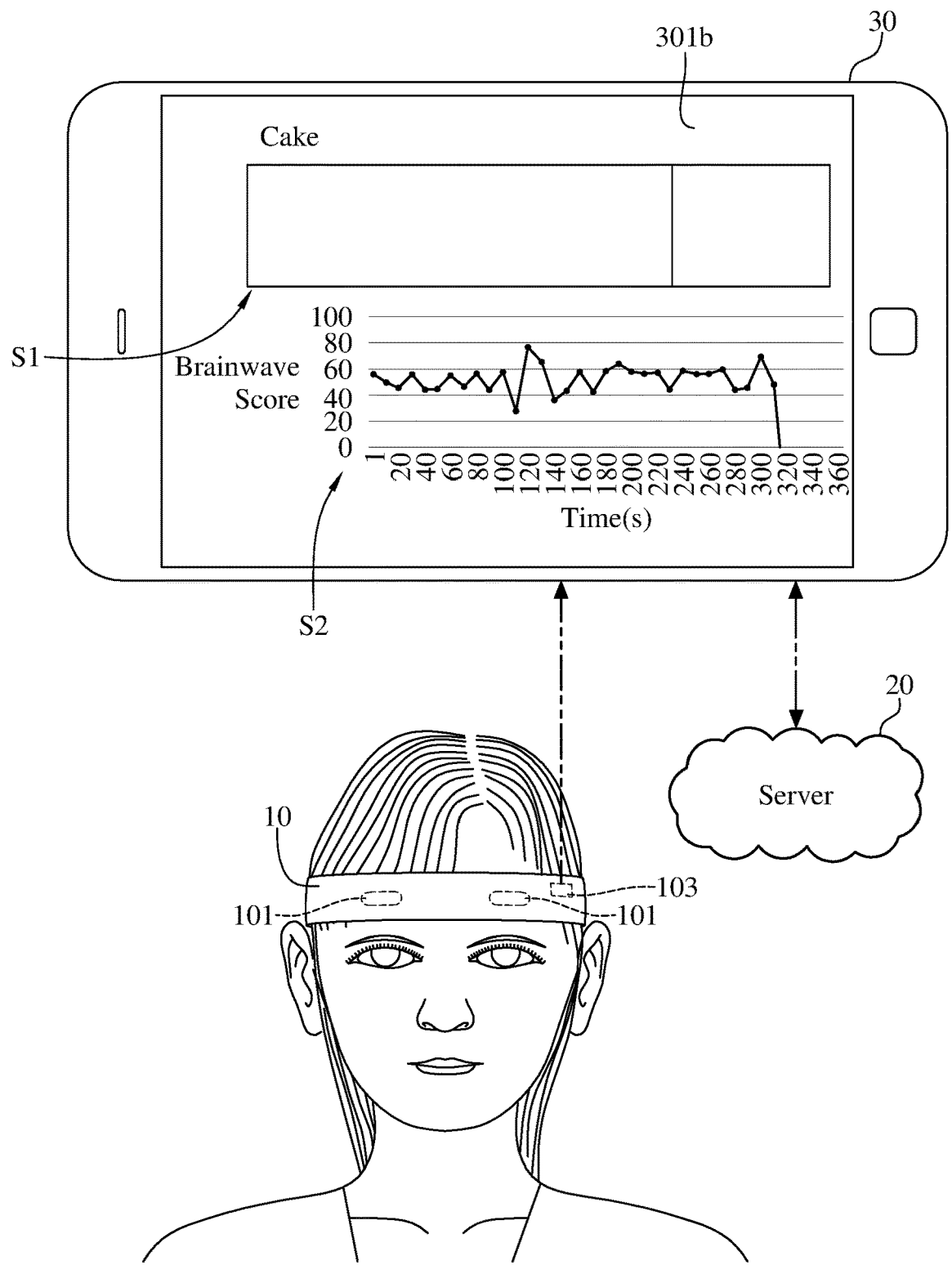

Please refer to both FIGS. 5A and 5B, FIGS. 5A and 5B are diagrams of the scenarios of using the brainwave feedback system according to an embodiment of the present disclosure.

As shown in FIG. 5A, the brainwave sensing device 10 includes a dry electrode 101 configured to obtain the brainwave signal, and the dry electrode 101 preferably contacts the forehead of the user to obtain the brainwave signal of the prefrontal lobe. The server 20 is configured to perform the feedback procedure when the first physiological parameter falls outside of the predetermined parameter range, wherein the wireless transmitter 103 preferably is an internet transmitter which connects to the server 20, so that the server 20 can output the feedback keyword to the output component 301 using the wireless transmitter 103 (internet transmitter). Therefore, the feedback procedure can include outputting the feedback keyword in an audio form by using the headset 301a as the output component 301. In addition, the headset 301a can also be directly connected to the brainwave sensing device 10 to output the analysis result corresponding to the first brainwave signal in the audio form. The analysis result outputted in the audio form can be presented in different levels by using different volumes, clarity levels, times of presenting per unit time, wherein the analysis result is, for example, the brainwave score corresponding to the first brainwave signal, or the determined result of whether the first brainwave signals fits the predetermined standard.

Please continue referring to FIG. 5A, method of determining whether the physiological parameter falls within the predetermined parameter range by using the brainwave signal obtained at the prefrontal lobe is further described below. Specifically, the brainwave signals of humans are very different during different states such as opening the eyes, closing the eyes, staying awake, being asleep or even in a coma. According to the standard established by the International Organization of Societies for Electrophysiological Technology, the brainwave signal with different frequencies can be distinguished into α wave(8-12 Hz), β wave (12-40 Hz), δ wave (0.5-4 Hz), and θ wave (4-7 Hz).

After obtaining the brainwave signal at the prefrontal lobe, time-domain analysis and frequency domain analysis can be performed. In detail, for a brainwave signal in a period of time, time-domain analysis is performed through band-pass filter to preserve the brainwave signals that correspond to the designated brainwave frequency band, so as to analyze intensity and duration of the brainwave signal during that frequency band. Frequency domain analysis is performed with Fourier Transform and Wavelet Transform to dissect the brainwave signal in that period of time, and each of the dissected brainwave signals has a resolution of at least 1 Hz to estimate the intensity of the brainwave signal in the designated frequency domain, and the percentage of the brainwave signal with the designated frequency domain in the 1 Hz-40 Hz domain. That is, the mobile device 30 can transform the percentage of the designated frequency domain of the first physiological parameter in the 1 Hz-40 Hz domain to a ratio, and uses the ratio as the brainwave score.

Accordingly, the server 20 can determine whether the physiological parameter falls in the predetermined parameter range by using the brainwave signal obtained at the prefrontal lobe.

The scenarios of using the brainwave feedback system can also be as shown in FIG. 5B. After obtaining the first brainwave signal by the brainwave sensing device 10, the brainwave sensing device 10 can output the first brainwave signal to the mobile device 30 via the wireless transmitter 103. The mobile device 30 then can obtain the first physiological parameter based on the first brainwave signal, wherein the wireless transmitter 103 can be the internet transmitter as described above, the wireless transmitter 103 can also be a Bluetooth transmitter, the present disclosure is not limited thereto. The mobile device 30 can further display the feedback keyword "cake" as shown in the figure using the screen 301b of the output component 30 when the first physiological parameter falls outside of the predetermined parameter range.

In addition, the screen 301b can further display a bar graph S1, wherein the bar graph is configured to represent the first physiological parameter (the brainwave score). For example, when the first physiological parameter falls within the predetermined parameter range or is close to a median of the predetermined parameter range, the left column of the bar graph S1 takes up bigger area; when the first physiological parameter falls outside of the predetermined parameter range or is close to upper/lower limits of the predetermined parameter range, the area of the left column of the bar graph S1 decreases. The relative relationship between the first physiological parameter and the predetermined parameter range represented by the bar graph S1 can also be represented by the right column of the bar graph S1, the present disclosure is not limited thereto.

The output component 301b can also display a brainwave score-time graph S2 to represent the changes of the first physiological parameter in a time manner. That is, the time presented at the horizontal axis represents the time of obtaining each physiological parameter. When a physiological parameter falls within the predetermined parameter range or is close to a median of the predetermined parameter range, the brainwave score presented by the brainwave score-time graph S2 is higher. On the contrary, when a physiological parameter falls outside of the predetermined parameter range or is close to upper/lower limits of the predetermined parameter range, the brainwave score presented by the brainwave score-time graph S2 is lower. The "time" of the brainwave score-time graph S2 is shown in second(s) unit, however, the present disclosure does not limit the unit of the time shown in the brainwave score-time graph S2.

By using the bar graph S1 and the brainwave score-time graph S2, the user can be informed whether their brainwave signal is close to the brainwave signal in the relaxed state. And when the brainwave signal is not close to the brainwave signal in the relaxed state, the user can try imaging the above mentioned feedback keyword to help adjust the brainwave signal. It should be noted that, the bar graph S1 and the brainwave score-time graph S2 disclosed herein are exemplary representations, the relative relationship between the physiological parameters and the default parameter range can also be shown in formats such as a color variation of the bar graph, a pie chart of a table, the present disclosure is not limited thereto.

The one or more embodiments of the brainwave feedback system and operation method thereof of the present disclosure can be used not only to alleviate insomnia, but also be used in improving depression, epilepsy, drug abuse, compulsive disorder, learning disability, anger, anxiety, migraine, post-traumatic stress disorder (PTSD) and attention deficit/hyperactivity disorder (ADHD).

In view of the above description, the brainwave feedback system and operation method according to one or more embodiments of the present disclosure may help users reduce the frequency of taking sleeping pills or other medications of above mentioned syndromes to avoid problems such addiction and bioaccumulation caused by drugs. In addition, the brainwave feedback system and operation method according to one or more embodiments of the present disclosure may further avoid the stimulation presented by the sleep aid device which in turn causes sleeping disturbance when the user is falling asleep or trying to fall asleep. The brainwave feedback system of the present disclosure may be applied in a home environment, which means the timing and places of using the brainwave feedback system are not limited. Therefore, the users don't have to visit specific research institute, such as a hospital, to use the brainwave feedback system. The users may use the brainwave feedback system consciously during their daily routines. Therefore, users can apply the experiences gained from training when they are trying to fall asleep to achieve the effect of falling asleep quickly, thereby avoiding the situation of using external assistance to help users fall asleep.

The present disclosure has been disclosed above in the embodiments described above, however it is not intended to limit the present disclosure. It is within the scope of the present disclosure to be modified without deviating from the essence and scope of it. It is intended that the scope of the present disclosure is defined by the following claims and their equivalents.

What is claimed is:

1. A brainwave feedback system, adapted to generate feedback based on a user's brainwave, the brainwave feedback system comprising:
   a brainwave sensing device, configured to obtain a first brainwave signal of the user;
   a server, storing a keyword string pool including a plurality of sorted keywords, and performing a feedback procedure when a first physiological parameter falls outside of a predetermined parameter range, wherein the first physiological parameter is associated with the first brainwave signal, and the feedback procedure includes choosing a keyword from the keyword string pool by the server as a feedback keyword and outputting the feedback keyword; and
   an output component, in communicable connection with the server, wherein the output component presents an analysis result corresponding to the first physiological parameter and presents the feedback keyword,
   wherein the brainwave sensing device obtains a second brainwave signal of the user after the output component presents the feedback keyword, and whether to increase an intensity of the output component presenting the feedback keyword is determined based on a comparison result between the first physiological parameter and a second physiological parameter associated with second brainwave signal.

2. The brainwave feedback system according to claim 1, wherein comparing the first physiological parameter and the second physiological parameter to generate the comparison result, and determining whether to increase the intensity of the output component presenting the feedback keyword based on the comparison result is performed by the server.

3. The brainwave feedback system according to claim 1, wherein the server further selectively chooses another keyword from the keyword string pool as the feedback keyword based on the comparison result, and outputs the feedback keyword.

4. The brainwave feedback system according to claim 1, wherein the server is configured to obtain and sort the keywords to obtain the keyword string pool, and the server obtains and sorts the keywords by performing a language processing procedure on a reply and sorting the keywords according to a result of performing the language processing procedure on the reply, wherein the reply is obtained by the server from a mobile device.

5. The brainwave feedback system according to claim 4, wherein after the server performs the feedback procedure, the server further performs the language processing procedure on a feedback reply and updates a sequence of the keywords in the keyword string pool according to a result of performing the language processing procedure on the feedback reply, wherein the feedback reply is obtained by the server from the mobile device.

6. The brainwave feedback system according to claim 5, wherein the feedback reply comprises an emotion keyword, and the server performing the language processing procedure on the feedback reply and updating the sequence of the keywords in the keyword string pool according to the result of performing the language processing procedure on the feedback reply is: the server performing the language processing procedure on the feedback reply to capture the emotion keyword, and updating the sequence of the keywords in the keyword string pool according to the emotion keyword.

7. The brainwave feedback system according to claim 1, wherein the keyword string pool is stored in a user log of the server.

8. The brainwave feedback system according to claim 7, wherein the user log further stores a usage history, the server obtains a brainwave score according to the usage history as the analysis result, and the server obtains the brainwave score according to the usage history by increasing the brainwave score by a predetermined increment when a usage times in the usage history is lower than a threshold number, and not adjusting the brainwave score when the usage times in the usage history reaches the threshold number.

9. The brainwave feedback system according to claim 7, wherein the user log further stores a usage history, a mobile device obtains a brainwave score according to the usage history as the analysis result, the mobile device obtains the brainwave score according to the usage history by increasing the brainwave score by a predetermined increment when a usage times in the usage history is lower than a threshold number, and not adjusting the brainwave score when the usage times in the usage history reaches the threshold number.

10. The brainwave feedback system according to claim 1, further comprising a mobile device having the output component, wherein the mobile device is in communicable connection with the brainwave sensing device to receive the first brainwave signal, the mobile device analyzes the first physiological parameter to generate the analysis result.

11. The brainwave feedback system according to claim 10, wherein comparing the first physiological parameter and the second physiological parameter to generate the comparison result and determines, and determining whether to increase the intensity of the output component presenting the feedback keyword based on the comparison result is performed by the mobile device.

12. The brainwave feedback system according to claim 10, wherein the mobile device further selectively chooses another keyword from the keyword string pool as the feedback keyword-based on the comparison result, and outputs the feedback keyword.

13. The brainwave feedback system according to claim 1, wherein the server is further configured to sort the keywords to obtain the keyword string pool, and the server sorting the keywords to obtain the keyword string pool is: the server obtaining a sleeping quality parameter from a sleeping sensor, and sorting the keywords according to the sleeping quality parameter to obtain the keyword string pool.

14. An operation method of brainwave feedback system, adapted to a brainwave feedback system, wherein the brainwave feedback system is configured to generate feedback based on a user's brainwave, and the brainwave feedback system comprises a mobile device, a server and a brainwave sensing device, with the operation method comprising:
  presenting a questionnaire by the mobile device and obtaining a reply corresponding to the questionnaire;
  performing a language processing procedure on the reply by the server to capture a plurality of keywords from the reply;
  sorting the keywords according to a result of the language processing procedure by the server to obtain a keyword string pool;
  obtaining a first brainwave signal of the user by the brainwave sensing device and outputting the first brainwave signal to the mobile device;
  obtaining a first physiological parameter corresponding to the first brainwave signal based on the first brainwave signal by the mobile device;
  determining whether the first physiological parameter falls outside of a predetermined parameter range by the mobile device; and
  performing a feedback procedure by the mobile device when determining the first physiological parameter falls outside of the predetermined parameter range,
  wherein the feedback procedure includes controlling the server by the mobile device to choose a keyword from the keyword string pool as a feedback keyword, and output the feedback keyword to the mobile device for the mobile device to present the feedback keyword,
  wherein after presenting the feedback keyword by the mobile device, the operation method further comprises:
    obtaining a second brainwave signal of the user by the brainwave sensing device;
    comparing the first physiological parameter and a second physiological parameter associated with the second brainwave signal by the mobile device to generate a comparison result; and
    determining whether to increase an intensity of an output component presenting the feedback keyword by the mobile device based on the comparison result.

15. The operation method according to claim 14, further comprising: updating the second physiological parameter by the mobile device based on the comparison result.

16. The operation method according to claim 14, wherein after generating the comparison result, the operation method further comprises:
  determining by the mobile device whether to choose another keyword from the keyword string pool as the feedback keyword by the server, and outputting the feedback keyword.

17. The operation method according to claim 14, wherein after performing the feedback procedure by the mobile device, the operation method further comprises:

presenting a feedback questionnaire by the mobile device and obtaining a feedback reply corresponding to the feedback questionnaire; and performing the language processing procedure on the feedback reply by the server to update a sequence of the keywords in the keyword string pool.

18. The operation method according to claim 17, wherein the feedback reply comprises an emotion keyword, and performing the language processing procedure on the feedback reply and updating the sequence of the keywords in the keyword string pool according to the result of performing the language processing procedure on the feedback reply is:

performing the language processing procedure on the feedback reply to capture the emotion keyword; and updating the sequence of the keywords in the keyword string pool according to the emotion keyword.

19. The operation method according to claim 14, wherein before obtaining the first brainwave signal by the brainwave sensing device, the operation method further comprises: presenting the feedback keyword by the mobile device.

20. The operation method according to claim 14, wherein sorting the keywords according to the result of the language processing procedure by the server to obtain the keyword string pool comprises:

obtaining a sleeping quality parameter from a sleeping sensor; and sorting the keywords according to the sleeping quality parameter to obtain the keyword string pool.

* * * * *